United States Patent
Nakamura

(10) Patent No.: US 10,927,270 B2
(45) Date of Patent: Feb. 23, 2021

(54) OIL-BASED INK COMPOSITION FOR WRITING INSTRUMENTS, AND WRITING INSTRUMENT, MARKING PEN AND BALLPOINT PEN COMPRISING THE SAME

(71) Applicant: KABUSHiKI KAISHA PILOT CORPORATION, Tokyo (JP)

(72) Inventor: Hisashi Nakamura, Aichi-ken (JP)

(73) Assignee: KABUSHIKI KAISHA PILOT CORPORATION, Toyko (JP)

( * ) Notice: Subject to any disclaimer, the term of this patent is extended or adjusted under 35 U.S.C. 154(b) by 393 days.

(21) Appl. No.: 15/575,855

(22) PCT Filed: May 25, 2016

(86) PCT No.: PCT/JP2016/065400
§ 371 (c)(1),
(2) Date: Nov. 21, 2017

(87) PCT Pub. No.: WO2016/190334
PCT Pub. Date: Dec. 1, 2016

(65) Prior Publication Data
US 2018/0127609 A1  May 10, 2018

(30) Foreign Application Priority Data
May 28, 2015  (JP) .............................. JP2015-108118

(51) Int. Cl.
| | | |
|---|---|---|
| C09D 11/00 | (2014.01) |
| C09D 11/18 | (2006.01) |
| C09D 11/16 | (2014.01) |
| B43K 7/00 | (2006.01) |
| B43K 8/02 | (2006.01) |
| C07C 39/16 | (2006.01) |
| C07H 13/06 | (2006.01) |
| C08G 6/00 | (2006.01) |
| C09D 11/17 | (2014.01) |
| C09D 1/00 | (2006.01) |
| C09D 4/00 | (2006.01) |
| C09D 5/00 | (2006.01) |
| C09K 3/00 | (2006.01) |

(52) U.S. Cl.
CPC ............... *C09D 11/18* (2013.01); *B43K 7/00* (2013.01); *B43K 8/02* (2013.01); *C07C 39/16* (2013.01); *C07H 13/06* (2013.01); *C08G 6/00* (2013.01); *C09D 11/16* (2013.01); *C09D 11/17* (2013.01)

(58) Field of Classification Search
USPC .......... 106/31.01, 31.13, 31.27, 31.57, 31.58
See application file for complete search history.

(56) References Cited

U.S. PATENT DOCUMENTS

2015/0090159 A1* 4/2015 Wang ...................... C09B 11/24
106/494

FOREIGN PATENT DOCUMENTS

| EP | 2 772 523 | 9/2014 | |
|---|---|---|---|
| JP | 2001-200186 | 7/2001 | |
| JP | 2005-126491 | 5/2005 | |
| JP | 2009-292935 | 12/2009 | |
| JP | 2010-106052 | 5/2010 | |
| JP | 2010-241867 | 10/2010 | |
| JP | 2010-2754/9 | 12/2010 | |
| JP | 2011-080025 | 4/2011 | |
| JP | 2012-67210 | 4/2012 | |
| JP | 2012-82283 | 4/2012 | |
| JP | 2012-214611 | 11/2012 | |
| JP | 2014-141664 | 8/2017 | |
| WO | WO-2015033750 A1 * | 3/2015 | ............. C09D 11/17 |

OTHER PUBLICATIONS

Communication pursuant to Article 94(3) EPC dated Nov. 15, 2019 in corresponding European Patent Application No. 16800038.8.
International Search Report dated Jul. 5, 2016 in International (PCT) Application No. PCT/JP2016/065400.
Extended European Search Report dated Oct. 23, 2018 in corresponding European Application No. 16800038.8.
International Preliminary Report on Patentability dated Nov. 28, 2017 in International (PCT) Application No. PCT/JP2016/065400.
Office Action dated Sep. 9, 2019 in corresponding Singaporean Patent Application No. 11201709287X.
Office Action dated Oct. 4, 2018 in corresponding Singapore Patent Application No. 11201709287X.

(Continued)

*Primary Examiner* — James E McDonough
(74) *Attorney, Agent, or Firm* — Wenderoth, Lind & Ponack, L.L.P.

(57) ABSTRACT

An oil-based ink composition for a writing instrument, comprising a dye, an organic solvent and a phenolic compound of the following general formula (1):

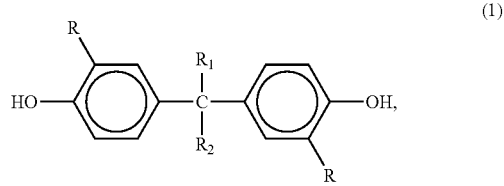

(1)

wherein R is each independently hydrogen or an alkyl group having 1 to 5 carbon atoms, $R_1$ is any of an alkyl group having 1 to 5 carbon atoms, a halogenated alkyl group having 1 to 5 carbon atoms, a phenyl group, a hydroxyphenyl group, and an alkyl group having 1 to 5 carbon atoms substituted by a hydroxyphenyl group, and $R_2$ is any of a halogenated alkyl group having 1 to 5 carbon atoms, a phenyl group, a hydroxyphenyl group, and an alkyl group having 1 to 5 carbon atoms substituted by a hydroxyphenyl group. The oil-based ink composition for a writing instrument can form handwriting having excellent water resistance in which no bleeding occurs on written surfaces of various materials with a dye retaining color development.

12 Claims, No Drawings

(56) References Cited

OTHER PUBLICATIONS

Notice of Reasons for Refusal dated Oct. 25, 2019 in corresponding Japanese Patent Application No. 2017-520729, with machine translation.

Office Action dated Dec. 12, 2019 in Taiwanese Patent Application No. 105116736, with English-language translation.

Jian Song et al., "Microencapsulation Technology and Application", Beijing: Chemical Industry Press, First Edition, Sep. 2001, 10 pages, with English translation.

* cited by examiner

OIL-BASED INK COMPOSITION FOR WRITING INSTRUMENTS, AND WRITING INSTRUMENT, MARKING PEN AND BALLPOINT PEN COMPRISING THE SAME

BACKGROUND OF THE INVENTION

Field of the Invention

The present invention relates to an oil-based ink composition for a writing instrument, and a writing instrument, a marking pen and a ballpoint pen comprising the oil-based ink composition. More particularly, the present invention relates to an oil-based ink composition for a writing instrument which can form handwriting having excellent water resistance, and a writing instrument, a marking pen and a ballpoint pen comprising the oil-based ink composition.

Background Art

A dye is conventionally contained as a coloring agent into an oil-based ink composition because of excellent color development, but an oil-based ink composition including a dye is prone to lower water resistance so that bleeding of handwriting in which the ink composition bleeds from handwriting to spread to the circumference occurs by adhesion of water. Taking this problem into consideration, though a metallized dye is included into an ink composition and an amount of a resin to be included into an ink composition is increased, an ink composition including the metallized dye is not sufficient for color development and an ink composition including the increased amount of resin is highly viscous and therefore there was still room for improvement in the writing performance.

To solve the problems as described above, additions of various compounds are investigated, for example, inclusion of a sucrose fatty acid ester having HLB value of not more than 8 or a sucrose fatty acid ester having HLB value of 9 to 11 into an ink composition is suggested (see e.g. Patent Documents 1 and 2).

However, even when a sucrose fatty acid ester had a specific HLB value, there was not sufficient effect depending on a kind of dye to be used, a material of surface to be written, and the like so that water resistance of handwriting could not be improved.

Especially, when a surface to be written is a paper, handwriting is prone to bleed and spread around the handwriting by adhesion of water, which results in extremely poor appearance of the handwriting. Therefore, there is a need for an oil-based ink composition which can form handwriting capable to prevent the occurrence of bleeding and having excellent water resistance even when a surface to be written is a paper.

RELATED ART DOCUMENTS

Patent Documents

Patent Document 1: JP-A-2001-200186
Patent Document 2: JP-A-2012-214611

SUMMARY OF THE INVENTION

Problems to be Solved by the Invention

Thus, an object of the present invention is to provide an oil-based ink composition for a writing instrument which can form handwriting having excellent water resistance so that adhesion of water does not cause bleeding on written surfaces of various materials though the oil-based ink includes a dye.

Means for Solving the Problems

An oil-based ink composition for a writing instrument of the present invention is characterized by comprising a dye, an organic solvent, and a phenolic compound of the following general formula (1):

[Chem 1]

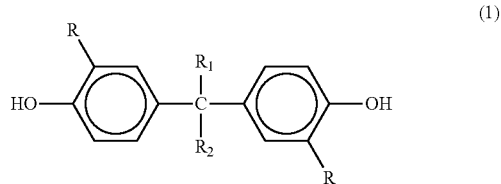

(1)

[wherein R is each independently hydrogen or an alkyl group having 1 to 5 carbon atoms, $R_1$ is any of an alkyl group having 1 to 5 carbon atoms, a halogenated alkyl group having 1 to 5 carbon atoms, a phenyl group, a hydroxyphenyl group, and an alkyl group having 1 to 5 carbon atoms, substituted by a hydroxyphenyl group, and $R_2$ is any of a halogenated alkyl group having 1 to 5 carbon atoms, a phenyl group, a hydroxyphenyl group, and an alkyl group having 1 to 5 carbon atoms, substituted by a hydroxyphenyl group]

A writing instrument of the present invention is characterized by comprising an oil-based ink composition for a writing instrument described above.

Effects of the Invention

According to an oil-based ink composition for a writing instrument of the present invention, handwriting having excellent water resistance can be formed in which no bleeding occurs on written surfaces of various materials with a dye retaining color development. Especially, handwriting having excellent water resistance can be formed in which no bleeding occurs even on a written surface whose material is a paper prone to bleeding of handwriting.

Moreover, according to an oil-based ink composition for writing instruments of the present invention, a writing instrument comprising an oil-based ink composition for a writing instrument which has excellent convenience and high practicality can be provided.

DETAILED DESCRIPTION OF THE INVENTION (Oil-Based Ink Compositions for Writing Instruments)

An oil-based ink composition for a writing instrument of the present invention (hereinafter simply referred to as "ink composition") is characterized by comprising at least a dye, an organic solvent and a phenolic compound of the general formula (1) below. As a writing instrument using the ink composition according to the present invention, it is not particularly limited, and use for a marking pen is preferable from the viewpoint of feeling of writing.

(Phenolic Compounds)

The phenolic compound included in the ink composition of the present invention is a compound which includes two or more phenol groups as represented by the general formula (1) below, and can interact with a dye in the ink composition to prevent dissolution of the dye in water because of having specific strong electron donating substituents, $R_1$ and $R_2$. In other words, water resistance of handwriting can be improved to prevent occurrence of bleeding caused by adhesion of water or the like. This effect acts effectively on a solvent dye (also referred to as an oil-soluble dye) made from a basic dye which especially has poor water resistance so that distinct handwriting difficult to bleed in water can be formed regardless of dye type.

[Chem 2]

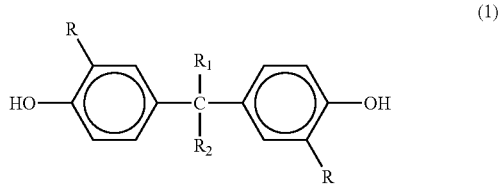

(1)

In the general formula (1) above, R is each independently hydrogen or an alkyl group having 1 to 5 carbon atoms, preferably H or an alkyl group having 1 to 3 carbon atoms, more preferably hydrogen or methyl group.

In the general formula (1) above, $R_1$ is any of an alkyl group having 1 to 5 carbon atoms, a halogenated alkyl group having 1 to 5 carbon atoms, a phenyl group, a hydroxyphenyl group, and an alkyl group having 1 to 5 carbon atoms substituted by a hydroxyphenyl group, preferably any of an alkyl group having 1 to 3 carbon atoms, a halogenated alkyl group having 1 to 3 carbon atoms, a phenyl group, a hydroxyphenyl group, and an alkyl group having 1 to 5 carbon atoms substituted by a hydroxyphenyl group, more preferably any of a methyl group, a halogenated alkyl group, a phenyl group, a hydroxyphenyl group and an alkyl group having 1 to 5 carbon atoms substituted by a hydroxyphenyl group.

In the general formula (1) above, $R_2$ is any of a halogenated alkyl group having 1 to 5 carbon atoms, a phenyl group, a hydroxyphenyl group, and an alkyl group having 1 to 5 carbon atoms substituted by a hydroxyphenyl group, preferably any of a halogenated alkyl group having 1 to 3 carbon atoms, a phenyl group, a hydroxyphenyl group, and an alkyl group having 1 to 5 carbon atoms substituted by a hydroxyphenyl group, more preferably any of a halogenated methyl group, a phenyl group, hydroxyphenyl group, and an alkyl group having 1 to 5 carbon atoms substituted by a hydroxyphenyl group.

Examples of compounds following the general formula (1) above include bisphenolic compounds, trisphenol, and tetrakisphenol, which may have R, $R_1$ and/or $R_2$ as substituents. More specifically, they include, for example, 4,4'-(1-α-methylbenzylidene)bisphenol, 4,4'-(1-phenylethane-1,1-diyl)bis(2-methyl phenol), 2,2-bis(4-hydroxyphenyl) hexafluoropropane, 4,4'-dihydroxytetraphenylmethane, 1,1,1-tris(4-hydroxyphenyl)ethane, 4,4'-[4-(4-hydroxyphenyl) butane-2,2-diyl]diphenol, and 4,4'-[3-(4-hydroxyphenyl)-1-methylpropylidene]bis(2-methylphenol).

The content of the phenolic compound in the ink composition of the present invention is preferably 0.5 to 10% by mass, more preferably 1 to 8% by mass, based on the total mass of the ink composition.

When the content of the phenolic compound falls within the numerical range as described above, water resistance of handwriting formed with the ink composition of the present invention can be improved.

(Dyes)

Examples of dyes included in the ink composition of the present invention include organic solvent-soluble dyes categorized as solvent dyes in the Color Index, basic dyes, acid dyes, direct dyes and food dyes. The ink composition may include two or more types of these dyes.

Typically, basic dyes are high water-soluble so that handwriting formed with an ink composition including a solvent dye or the like including a basic dye as a component is prone to bleed due to adhesion of water. However, according to the oil-based ink composition of the present invention, occurrence of bleeding is prevented due to improved water resistance of handwriting.

Specific examples of solvent dyes include VALIFAST BLACK 3806 (C.I. Solvent Black 29), VALIFAST BLACK 3807 (a trimethylbenzylammonium salt of C.I. Solvent Black 29), SPIRIT BLACK SB (C.I. Solvent Black 5), Spiron Black GMH (C.I. Solvent Black 43), Nigrosine Base EX (C.I. Solvent Black 7), Spiron Pink BH (C.I. Solvent Red 82), Neozapon Blue 808 (C.I. Solvent Blue 70), Spiron Violet CRH (C.I. Solvent Violet 8-1), VALIFAST RED 1308 (a salt-forming body of C.I. Basic Red 1 and C.I. Acid Yellow 23), VALIFAST RED 1320, SPIRIT RED 102 (a salt-forming body of C.I. Basic Red 1 and C.I. Acid Yellow 42), VALIFAST VIOLET 1701 (a salt-forming body of C.I. Basic Violet 1 and C.I. Acid Yellow 42), VALIFAST VIOLET 1702 (a salt-forming body of C.I. Basic Violet 3 and C.I. Acid Yellow 36), Spiron Red CGH (a salt-forming body of C.I. Basic Red 1 and dodecyl(sulfophenoxy)benzenesulfonic acid), Spiron Yellow C-GNH and Oil Blue 613 (a mixture of C.I. Solvent Blue 5 and a resin).

Specific examples of basic dyes include C.I. Basic Orange 2, C.I. Basic Orange 14, C.I. Basic Green 4, C.I. Basic Blue 9, C.I. Basic Blue 26, C.I. Basic Violet 1, C.I. Basic Violet 3 and C.I. Basic Violet 10.

Specific examples of acid dyes include C.I. Acid Red 18, C.I. Acid Red 51, C.I. Acid Red 52, C.I. Acid Red 87, C.I. Acid Red 92, C.I. Acid Red 289, C.I. Acid Orange 10, C.I. Acid Yellow 3, C.I. Acid Yellow 7, C.I. Acid Yellow 23, C.I. Acid Yellow 42, C.I. Acid Green 3, C.I. Acid Green 16, C.I. Acid Blue 1, C.I. Acid Blue 9, C.I. Acid Blue 22, C.I. Acid Blue 90, C.I. Acid Blue 239, C.I. Acid Blue 248, C.I. Acid Violet 15, C.I. Acid Violet 49, C.I. Acid Black 1 and C.I. Acid Black 2.

Specific examples of direct dyes include C.I. Direct Red 28, C.I. Direct Yellow 44, C.I. Direct Blue 86, C.I. Direct Blue 87, C.I. Direct Violet 51 and C.I. Direct Black 19.

Specific examples of food dyes include C.I. Food Yellow 3 and C.I. Food Black 2.

The content of the dye in the ink composition of the present invention is preferably 3 to 40% by mass based on the total mass of the ink composition.

(Organic Solvents)

Conventional general-purpose solvent can be employed as an organic solvent included in the ink composition of the present invention. The ink composition may also include two or more types of organic solvents.

Specific examples of organic solvents include benzyl alcohol, ethylene glycol, diethylene glycol, propylene glycol, benzyl glycol, ethylene glycol monobutyl ether, ethylene glycol monohexyl ether, ethylene glycol monophenyl ether, diethylene glycol monoethyl ether, diethylene glycol monophenyl ether, propylene glycol monomethyl ether, propylene glycol monoethyl ether, propylene glycol monophenyl ether, dipropylene glycol monoethyl ether, dipropylene glycol monophenyl ether, tripropylene glycol monomethyl ether, tripropylene glycol monoethyl ether, tripropylene glycol monophenyl ether, methyl lactate, ethyl lactate and γ-butyrolactone.

In one embodiment, it is particularly preferable to use such an organic solvent that the vapor pressure thereof is 5.0 to 50 mmHg, more preferably 10 to 50 mmHg, at 20° C. which is a volatile temperature of organic solvents. Such an organic solvent is particularly preferable when a writing instrument comprising the ink composition is a marking pen.

Use of an organic solvent having such a vapor pressure can improve drying property of handwriting. Therefore, good handwriting can be formed without drawback such as adhesion of undried ink onto one's hand or staining blank parts having no handwriting on a written surface when one touches handwriting by hand.

Examples of organic solvents whose vapor pressure is 5.0 to 50 mmHg at 20° C. include alcoholic organic solvents such as ethyl alcohol (45), n-propyl alcohol (14.5), isopropyl alcohol (32.4), n-butyl alcohol (5.5), isobutyl alcohol (8.9), sec-butyl alcohol (12.7), tert-butyl alcohol (30.6), and tert-amyl alcohol (13.0); glycol ether-based organic solvents such as ethylene glycol monomethyl ether (8.5), ethylene glycol diethyl ether (9.7), ethylene glycol monoisopropyl ether (6.0), propylene glycol monomethyl ether (7.6), and propylene glycol monoethyl ether (10.6); hydrocarbon-based organic solvents such as n-heptane (35.0), n-octane (11.0), isooctane (41.0), methylcyclohexane (37.0), ethylcyclohexane (10.0), toluene (24.0), xylene (5.0 to 6.0), and ethylbenzene (7.1); ketone-based organic solvents such as methyl isobutyl ketone (16.0), methyl n-propyl ketone (12.0), methyl n-butyl ketone (12.0), and di-n-propyl ketone (5.2); and ester-based organic solvents such as n-butyl formate (22.0), isobutyl formate (33.0), n-propyl acetate (25.0), isopropyl acetate (48.0), n-butyl acetate (8.4), isobutyl acetate (13.0), ethyl propionate (28.0), n-butyl propionate (45.0), methyl butyrate (25.0), and ethyl butyrate (11.0).

Note that the numbers in parentheses indicate the vapor pressure of each organic solvent at 20° C.

Among the aforementioned organic solvents, from the viewpoints of quick-drying property of handwriting and solubility of resins and additives which may be used, alcohols having not more than 4 carbon atoms and/or glycol ethers having not more than 4 carbon atoms are more preferable, and ethyl alcohol, n-propyl alcohol, isopropyl alcohol, ethylene glycol monomethyl ether, ethylene glycol diethyl ether, ethylene glycol monoisopropyl ether, propylene glycol monomethyl ether, and propylene glycol monoethyl ether are still more preferable.

In one embodiment, it is preferable that the ink composition of the present invention comprise an organic solvent having a boiling point of 160 to 250° C.

An organic solvent having such a relatively high boiling point is preferable when a writing instrument comprising the ink composition is a ballpoint pen.

Whitening of a handwriting which is prone to occur under high humidity environment can be suppressed by including such an organic solvent having such a relatively high boiling point into the ink composition which is used being included in a marking pen or the like to adjust a drying rate of handwriting. Especially, it is preferable to adjust the drying rate by using an organic solvent having such a high boiling point when an organic solvent having a vapor pressure at 20° C. of 5.0 to 50 mmHg such as an alcohol having not more than 3 carbon atoms and/or a glycol ether having not more than 4 carbon atoms.

Especially, in accordance with the present invention, the ink composition comprises a phenolic compound, which may result in more likelihood to whiten handwriting when the handwriting is dried under high humidity environment than conventional ink compositions. Therefore, it is particularly preferable to include an organic solvent having such a high boiling point.

Examples of organic solvents having high boiling points include benzyl alcohol (205), ethylene glycol monophenyl ether (245), propylene glycol n-butyl ether (170), dipropylene glycol methyl ether (190), propylene glycol diacetate (190), dipropylene glycol dimethyl ether (175), dipropylene glycol n-propyl ether (212), dipropylene glycol methyl ether acetate (209), propylene glycol phenyl ether (243), tripropylene glycol methyl ether (242), dipropylene glycol n-butyl ether (229), tripropylene glycol n-butyl ether (274), p-xylene glycol dimethyl ether (235), benzyl formate (201), benzyl acetate (212), benzyl propionate (222), benzyl butyrate (240) and benzyl isobutyrate (230).

Note that the numbers in parentheses indicate the boiling point (Celsius) of each organic solvent.

The content of the organic solvent in the ink composition of the present invention is preferably 40 to 80% by mass based on the total mass of the ink composition.

The content of the aforementioned organic solvent having a vapor pressure at 20° C. of 5.0 to 50 mmHg is preferably not less than 50% by mass, more preferably not less than 70% by mass, based on the total mass of the organic solvents.

The content of aforementioned organic solvent having a high boiling point is preferably 1 to 10% by mass, more preferably 2 to 8% by mass, based on the total mass of the organic solvents.

(Optional Components)

The ink composition of the present invention may include optional components as follows.

(Resins)

The ink composition of the present invention may include a resin. This can improve water resistance of handwriting more. Additionally, not only can it improve fixability of handwriting, but it can impart fastness and the like. The ink composition of the present invention may include two or more types of resins.

The resins which can be employed are not particularly limited as long as they are soluble in an organic solvent included in the ink composition, and examples of the resins include ketone resins, amide resins, alkyd resins, rosin-modified resins, rosin-modified phenol resins, phenol resins, xylene resins, polyvinyl butyral resins, terpene-based resins, coumarone-indene resins, polyethylene oxide, poly(meth-acrylate), ketone-formaldehyde resins, α- and β-pinene-phenol condensation resins, polyvinyl butyral resins, maleic acid resins, acrylic resins and acrylic acid-methacrylic acid copolymers.

Among these, ketone resins are particularly preferable because fixability of handwriting can be improved so that peeling of the handwriting does not occur even when the handwriting is abraded in a state in which hand fat is adhered on it, even if the handwriting has been formed on non-permeable writing surface in combination with a phenolic compound of the general formula (1).

The content of the resin in the ink composition of the present invention is preferably 0.5 to 40% by mass, more preferably 1 to 35% by mass, based on the total mass of the ink composition.

(Sucrose Fatty Acid Esters)

The ink composition of the present invention may include a sucrose fatty acid ester. This can prevent evaporating of solvents out of the pen tip of a writing instrument including the ink composition of the present invention to form good handwriting without blur or the like even after the pen tip has been exposed to the outside air for a long time. Especially, in accordance with the present invention, the ink composition includes a phenolic compound, which may cause that the viscosity of ink at a nib tip increases extremely and the ink tends to be solidified by evaporation of solvents from the pen tip. Therefore, it is particularly preferable to include a sucrose fatty acid ester.

The HLB of a sucrose fatty acid ester to be used is preferably 8 to 18, more preferably 9 to 15. When the HLB of a sucrose fatty acid ester falls within the numerical range as described above, evaporation of a solvent from a pen tip can be prevented.

The content of the sucrose fatty acid ester in the ink composition of the present invention is preferably 0.5 to 5% by mass, more preferably 0.5 to 3% by mass, based on the total mass of the ink composition.

(Pigments)

The ink composition of the present invention may include a pigment. Examples of the pigments include carbon black, inorganic pigments such as ultramarine and titanium dioxide, organic pigments such as azo pigments, phthalocyanine pigments, indigo pigments, thioindigo pigments, threne pigments, quinacridone pigments, anthraquinone pigments, throne pigments, diketopyrrolopyrrole pigments, dioxazine pigments, perylene pigments, perinone pigments and isoindolinone pigments, metallic pigments such as aluminum powder and aluminum powder whose surface is treated with a colored resin, metallic luster pigments prepared by forming metal evaporated film on transparent or colored transparent films, fluorescent pigment, luminous pigments, and pearl pigments prepared by coating surfaces of natural mica, synthetic mica, glass pieces, alumina and transparent film pieces as core materials with metal oxides of titanium or the like.

(Light-Resistance Imparting Agents)

The ink composition of the present invention may include a light-resistance imparting agent. This can improve light resistance of handwriting and preferably prevent bleaching of a dye to form excellent light-resistant handwriting having a desired various color tone even when a mixed dye or salt-forming dye of a basic dye and an acid dye is used as a dye.

As light-resistance imparting agents, for example, benzotriazole derivatives such as 2-(3-t-butyl-5-octyloxycarbonylethyl-2-hydroxyphenyl)benzotriazole can be employed.

(Shear-Thinning Imparting Agents)

The ink composition of the present invention may include a shear-thinning imparting agent. This can further suppress occurrence of bleeding in handwriting. Thus, even when the material of written surface is paper or fabric material such as high permeable fabric, occurrence of bleeding in handwriting can be suppressed.

A shear-thinning imparting agent is particularly preferable when a writing instrument including the ink composition is a ballpoint pen. This can prevent leakage of ink from a gap between a ball and nib when not in use and prevent the backflow of ink when leaving the writing tip in a position in which the writing tip thereof is upward (in an upright position).

Examples of the shear-thinning imparting agents include crosslinked acrylic resins, emulsion types of crosslinked acrylic resins, non-crosslinked acrylic resins, crosslinked N-vinylcarboxylic acid amide polymer or copolymer, hydrogenated castor oil, fatty acid amide wax, waxes such as polyethylene oxide wax, metal salts of fatty acids such as aluminum salts of stearic acid, palmitic acid, octylic acid and lauric acid, dibenzylidene sorbitol, N-acylamino acid compounds, smectite-based inorganic compounds, montmorillonite-based inorganic compounds, bentonite-based inorganic compounds and hectorite-based inorganic compounds.

Note that the ink composition of the present invention may include two or more types of shear-thinning imparting agents.

(Lubricants)

The ink composition of the present invention may include a lubricant. When a writing instrument including the ink composition is a ballpoint pen, the ink composition includes a lubricant, thereby able to prevent wear on contacting parts of the ball receiving seat and ball to improve durability of the ballpoint pen.

Examples of the lubricants include higher fatty acids such as oleic acid, nonionic surfactants having long chain alkyl groups, polyether-modified silicone oils, phosphate ester-based surfactants, fluorochemical surfactants, silicone-based surfactants, fatty acid alkanolamides, anionic surfactants, cationic surfactants, ampholytic surfactants, or metal salts, ammonium salts, amine salts, or alkanolamine salts thereof.

Among the aforementioned lubricants, phosphate ester-based surfactants are particularly preferable because wear of a ball receiving seat and ball can be prevented more.

Examples of the phosphate ester-based surfactants include thiophosphite triesters such as tri(alkoxycarbonylmethyl) thiophosphites and tri(alkoxycarbonylethyl) thiophosphites, phosphate monoesters of polyoxyethylene alkyl ethers, polyoxyethylene alkylaryl ethers or the like, phosphate diesters of polyoxyethylene alkyl ethers, polyoxyethylene alkylaryl ethers or the like, phosphate triesters, alkylphosphate esters or alkyl ether phosphate esters of polyoxyethylene alkyl ethers, polyoxyethylene alkylaryl ethers or the like, or derivatives thereof.

The number of carbon atoms of an alkyl group of the aforementioned phosphate esters is preferably 5 to 18, more preferably 10 to 15. Additionally, the number of carbon atoms of the alkyl group is preferably 12 to 18 when taking temporal stability of the ink composition into consideration.

Additionally, commercially available phosphate ester-based surfactants may be used, and include, for example, PLYSURF A217E (the carbon number of the alkyl group: 14, the acid value: 45 to 58), PLYSURF A219B (the carbon number of the alkyl group: 12, the acid value: 44 to 58), PLYSURF A215C (the carbon number of the alkyl group: 12, the acid value: 135 to 155), and PLYSURF A208N (the carbon number of the alkyl group: a mixture of 12 and 13, the acid value: 15 to 58), manufactured by DKS Co., Ltd., and Phosphanol RB-410 (the carbon number of the alkyl group: 18, the acid value: 80 to 90), Phosphanol RS-610 (the carbon number of the alkyl group: 13, the acid value: 75 to 90), and Phosphanol RS-710 (the carbon number of the alkyl group: 13, the acid value: 55 to 75), manufactured by TOHO Chemical Industry Co., Ltd.

Note that the acid value is defined as a number of mg of potassium hydroxide required for neutralization of acidic constituent included in 1 gram of a sample and measured in conformity to JIS K 0070.

In this case, the content of a lubricant in the ink composition is preferably 0.1 to 5.0% by mass, more preferably 0.3 to 3.0% by mass, based on the total mass of the ink composition. When the content of a lubricant is within the numerical range described above, wear of a ball receiving seat and ball can be prevented more maintaining temporal stability of the ink composition.

(Stringiness Imparting Resins)

The ink composition of the present invention may include a stringiness imparting resin. When a writing instrument including the ink composition is a ballpoint pen, the ink composition includes a stringiness imparting resin, thereby able to improve integrity of the ink composition to suppress the excess ink at the nib tip.

Examples of the stringiness imparting resins include polyvinylpyrrolidone resins.

In this case, the content of a stringiness imparting resin in the ink composition is preferably 0.01 to 3.0% by mass, more preferably 0.1 to 2.0% by mass, based on the total mass of the ink composition. When the content of a stringiness imparting resin falls within the numerical range described above, the excess ink can be suppressed more effectively maintaining its solubility in the ink composition.

(Organic Amines)

When the ink composition includes a lubricant such as phosphate ester-based surfactants, it is preferable that the ink composition include an organic amine. The ink composition includes an organic amine, thereby able to neutralize the phosphate ester-based surfactant to improve temporal stability of the ink composition.

As organic amines, any of primary amines, secondary amines and tertiary amines can be employed, but it is preferable to use a secondary amine or a tertiary amine when taking the reactivity with components of the ink composition into consideration.

More specifically, oxyethylenealkylamines, polyoxyethylenealkylamines, laurylamine, stearylamine, distearylamine, dimethyllaurylamine, dimethylstearylamine, and dimethyloctylamine are preferable. Among these, oxyethylenealkylamines and polyoxyethylenealkylamines which have ethylene oxide structure ($CH_2CH_2O$) are preferable because wear of a ball receiving seat and ball can be prevented more when used in combination with a lubricant.

The total amine value of organic amines included in the ink composition of the present invention is preferably 70 to 300 mg KOH/g, more preferably 150 to 300 mg KOH/g, from the viewpoints of temporal stability.

Note that the total amine value is defined as a number of mg of potassium hydroxide equivalent to hydrochloric acid required for neutralization of 1 gram of a sample and measured in conformity to JIS K 7237.

Commercially available organic amines may be used, and include, for example, Nymeen L-201 (the total amine value: 232 to 246, a secondary amine), Nymeen L-202 (the total amine value: 192 to 212, a tertiary amine), Nymeen L-207 (the total amine value: 107 to 119, a tertiary amine), Nymeen S-202 (the total amine value: 152 to 166, a tertiary amine), Nymeen S-204 (the total amine value: 120 to 134, a tertiary amine), Nymeen S-210 (the total amine value: 75 to 85, a tertiary amine), and Nymeen DT-204 (the total amine value: 146 to 180, a tertiary amine), manufactured by Nippon Oils & Fats Co., Ltd., and FARMIN 80 (the total amine value: 204 to 210, a primary amine), FARMIN D86 (the total amine value: 110 to 119, a secondary amine), FARMIN DM2098 (the total amine value: 254 to 265, a tertiary amine), and FARMIN DM8680 (the total amine value: 186 to 197, a tertiary amine), manufactured by Kao Corporation.

In this case, the content of an organic amine in the ink composition is preferably 0.1 to 10.0% by mass, more preferably 0.5 to 5.0% by mass, based on the total mass of the ink composition.

Additionally, when the ink composition includes an organic amine and a phosphate ester-based surfactant as a lubricant, it is preferable to meet the formula: $0.1 \leq Y/X \leq 2.0$, wherein the total amine value of the organic amine is represented as X and the acid value of the phosphate ester-based surfactant is represented as Y, more preferably $0.1 \leq Y/X \leq 1.0$, still more preferably $0.3 \leq Y/X \leq 1.0$, and particularly preferably $0.3 \leq Y/X \leq 0.8$. The total amine value of the organic amine included in the ink composition and the acid value of the phosphate ester-based surfactant included in the ink composition meet the aforementioned relationship, thereby able to suppress the generation of deposits to prevent the occurrence of writing fault.

The ink composition of the present invention may further include a viscosity modifier, a coloring stabilizer, a plasticizer, a chelating agent, and a co-solvent such as water and/or the like.

(Writing Instruments)

The writing instrument of the present invention comprises the aforementioned ink composition.

The types of the writing instruments are not limited, but include, for example, marking pens, ballpoint pens and the like, wherein nibs are mounted onto the writing nibs.

The marking pens according to the present invention, with regard to structures and shapes of the marking pens themselves, are not particularly limited and include, for example, a marking pen having a structure in which a nib, such as a fabric nib, a felt nib or a plastic nib, is mounted onto the writing tip, and ink is impregnated into an ink absorbent body made of a fiber bundle housed inside a barrel and supplied to the writing tip; and a marking pen having a structure in which ink is placed directly inside a barrel of the same nib as above and supplied to the writing tip through an ink flow adjusting member including a comb groove-shaped ink flow adjusting member and a fiber bundle. Note that a metal workpiece such as resin moldings and aluminum cans is used as said barrel.

The ballpoint pens according to the present invention, with regard to structures and shapes of the ballpoint pens themselves, are not particularly limited and include, for example, a ballpoint pen having a structure in which ink is impregnated into an ink absorbent body made of a fiber bundle housed inside a barrel and supplied to a ballpoint pen nib wherein a ball is mounted onto the tip; a ballpoint pen having a structure in which ink is placed directly inside a barrel and supplied to a ballpoint pen nib through an ink flow adjusting member including a comb groove-shaped ink flow adjusting member and a fiber bundle; and a ballpoint pen having a structure in which an ink reservoir tube includes the ink composition inside a barrel, communicates with a ballpoint pen nib, and is close to liquid stopper for preventing backflow and optionally a solid ink backflow preventing body on the end surface of the ink inside the ink reservoir tube. Note that a resin molding and a metal workpiece are used as said barrel and ink reservoir tube.

Examples

[Water Resistance Test (No. 1)]

The ink compositions of examples and comparative examples are shown in the following Table. Note that the values of the compositions shown in the Table indicate parts by mass.

TABLE 1

|  | Note | Examples |  |  |  |  | Comparative examples |  |  |  |  |
|---|---|---|---|---|---|---|---|---|---|---|---|
|  |  | 1 | 2 | 3 | 4 | 5 | 1 | 2 | 3 | 4 | 5 |
| Black dye | (1) | 8.0 |  |  |  |  | 8.0 |  |  |  |  |
| Red dye | (2) |  | 7.0 |  |  | 7.0 |  | 7.0 |  |  | 7.0 |
| Blue dye | (3) |  |  | 4.0 |  |  |  |  | 4.0 |  |  |
| Yellow dye | (4) | 1.0 |  |  | 5.0 |  | 1.0 |  |  | 5.0 |  |
| Resin A | (5) | 7.0 | 7.0 | 5.0 | 5.0 | 7.0 | 7.0 | 7.0 | 5.0 | 5.0 | 7.0 |
| Resin B | (6) |  |  | 5.0 | 5.0 |  |  |  | 5.0 | 5.0 |  |
| Phenolic compound A | (7) | 1.0 |  |  |  | 5.0 |  |  |  |  |  |
| Phenolic compound B | (8) |  | 7.0 |  |  |  |  |  |  |  |  |
| Phenolic compound C | (9) |  |  | 2.0 |  |  |  |  |  |  |  |
| Phenolic compound D | (10) |  |  |  | 3.0 |  |  |  |  |  |  |
| Bisphenol A | (11) |  |  |  |  |  | 1.0 |  |  |  |  |
| Bisphenol F | (12) |  |  |  |  |  |  | 2.0 |  |  |  |
| Sucrose fatty acid ester A | (13) |  |  |  |  |  |  |  | 3.0 |  |  |
| Sucrose fatty acid ester B | (14) |  |  |  | 1.0 |  |  |  |  |  | 1.0 |
| Ethanol |  | 42.0 | 59.0 | 21.0 | 19.0 | 60.0 | 42.0 | 66.0 | 21.0 | 19.0 | 65.0 |
| n-Propanol |  | 21.0 |  | 43.0 | 43.0 |  | 21.0 |  | 43.0 | 43.0 |  |
| Propylene glycol monomethyl ether |  | 20.0 | 20.0 | 20.0 | 20.0 | 20.0 | 20.0 | 20.0 | 20.0 | 20.0 | 20.0 |

The source content shown in the Table will be described according to the note numbers.

(1) Trade name: NIGROSINE BASE EX, manufactured by Orient Chemical Industries Co., Ltd.

(2) Trade name: VALIFAST RED 1308, manufactured by Orient Chemical Industries Co., Ltd.

(3) Trade name: OIL BLUE 613, manufactured by Orient Chemical Industries Co., Ltd.

(4) Trade name: Spiron Yellow C-GNH, manufactured by Hodogaya Chemical Co., Ltd.

(5) Trade name: Ketone Resin K-90, manufactured by ARAKAWA CHEMICAL INDUSTRIES, LTD.

(6) Trade name: Rosin WW, manufactured by ARAKAWA CHEMICAL INDUSTRIES, LTD.

(7) Bisphenol, wherein R=H, $R_1$=$CH_3$, $R_2$=$C_6H_5$ in the general formula (1)

(8) Trisphenol, wherein R=$CH_3$, $R_1$=$CH_3$, $R_2$=$C_2H_4C_6H_5OH$ in the general formula (1)

(9) Bisphenol, wherein R=H, $R_1$=$R_2$=$CF_3$ in the general formula (1)

(10) Trisphenol, wherein R=H, $R_1$=$CH_3$, $R_2$=$C_6H_5OH$ in the general formula (1)

(11) Bisphenol, wherein R=H, $R_1$=$R_2$=$CH_3$ in the general formula (1)

(12) Bisphenol, wherein R=$R_1$=$R_2$=H in the general formula (1)

(13) Trade name: DK ESTER F-110 (HLB: 11), manufactured by DKS Co., Ltd.

(14) Trade name: RYOTO Sugar Ester S-570 (HLB: 5), manufactured by Mitsubishi-Chemical Foods Corporation Preparation of the Ink Compositions Each source was mixed in an amount of the loading as described in Table 1 above and stirred at 20° C. for 3 hours to dissolve to obtain the ink composition.

Making of Marking Pens

Each 5 g of the ink compositions obtained in the examples and comparative examples was stored into a commercially available marking pen exterior (PILOT CORPORATION; WMBM-12L, including a polyester nib) to obtain an oil-based marking pen.

Water Resistance Test

The water resistance tests with the marking pens made as mentioned above were carried out according to the following procedure in conformity to the water resistance test specified in JIS S6037 except the modification of the immersion time.

Writing by hand helicoidally was carried out on JIS P3201 writing paper A under the environment of 20° C., using each marking pen which was confirmed to be writable. Subsequently, the written papers were dipped into water for 30 minutes in such a manner that the handwriting was soaked, then removed and dried. After the drying, the states of the handwriting were checked visually, and evaluated according to the following criteria. Results of the evaluation are shown in Table 2 below.

The Criteria

A: No bleeding of handwriting occurs.

B: The dye from handwriting bled a little, or the whole paper and dipping liquid were faintly-stained.

C: The dye bled around handwriting, or the whole paper and dipping liquid were stained.

TABLE 2

|  | Examples |  |  |  |  | Comparative examples |  |  |  |  |
|---|---|---|---|---|---|---|---|---|---|---|
|  | 1 | 2 | 3 | 4 | 5 | 1 | 2 | 3 | 4 | 5 |
| Water resistance test | A | A | A | A | A | B | C | C | C | C |

[Water Resistance Test (No. 2)]

TABLE 3

| | Note | Examples | | | | Comparative examples | | |
|---|---|---|---|---|---|---|---|---|
| | | 6 | 7 | 8 | 9 | 6 | 7 | 8 |
| Dye 1 | (15) | 15.0 | | | 15.0 | 15.0 | | |
| Dye 2 | (16) | | 12.0 | | | | 12.0 | |
| Dye 3 | (17) | | | 12.0 | | | | 12.0 |
| Dye 4 | (18) | 7.0 | | | 7.0 | 7.0 | | |
| Resin C | (19) | 20.0 | 20.0 | | | 20.0 | 20.0 | |
| Resin D | (20) | | | 18.5 | 15.0 | | | 18.5 |
| Phenolic compound C | (9) | 5.0 | | 5.0 | | | | |
| Phenolic compound D | (10) | | 5.0 | | 5.0 | | | |
| Stringiness imparting resin | (21) | 0.5 | 0.5 | 0.5 | 0.5 | 0.5 | 0.5 | 0.5 |
| Lubricant A | (22) | 2.0 | 2.0 | 2.0 | | 2.0 | 2.0 | 2.0 |
| Lubricant B | (23) | | | 2.0 | 1.0 | | | 2.0 |
| Organic amine A | (24) | | 0.2 | 0.2 | 1.0 | | 0.2 | 0.2 |
| Organic amine B | (25) | 1.0 | | | | 1.0 | | |
| Benzyl alcohol | | 10.0 | 30.15 | 10.0 | 10.0 | 10.0 | 32.65 | 10.0 |
| Ethylene glycol monophenyl ether | | 39.5 | 30.15 | 49.8 | 45.5 | 44.5 | 32.65 | 54.8 |

The source content shown in the Table will be described according to the note numbers.

(15) Trade name: VALIFAST VIOLET 1705, manufactured by Orient Chemical Industries Co., Ltd.
(16) Trade name: VALIFAST RED 1308, manufactured by Orient Chemical Industries Co., Ltd.
(17) Trade name: VALIFAST RED 1320, manufactured by Orient Chemical Industries Co., Ltd.
(18) Trade name: Spiron Yellow C-GNH, manufactured by Hodogaya Chemical Co., Ltd.
(19) Ketone resin, Trade name: Hylak 110H, manufactured by Hitachi Chemical Company, Ltd.
(20) Butyral resin, Trade name: Eslek BL-1, manufactured by SEKISUI CHEMICAL CO., LTD.
(21) Trade name: Polyvinylpyrrolidone K-90, manufactured by ISP Japan Co., Ltd.
(22) Oleic acid
(23) Trade name: PLYSURF A208N, manufactured by DKS Co., Ltd.
(24) Trade name: Nymeen L201, Total amine value: 232 to 246, Secondary amine, manufactured by NOF CORPORATION
(25) Trade name: FARMIN DM2098, Total amine value: 254 to 265, Tertiary amine, manufactured by Kao Corporation Preparation of the Ink Compositions Each source was mixed in an amount of the loading as described in Table 3 above and heated to 60° C. before it was dissolved completely with a disper stirrer and allowed to cool at room temperature to obtain the ink composition.

Making of Ballpoint Pens

Each 0.2 g of the ink compositions obtained in the examples and comparative examples was stored into a commercially available ballpoint pen exterior (PILOT CORPORATION; BPS-GPN-F) including the ball having a ball diameter of φ3.0.7 mm to obtain a ballpoint pen.

Water Resistance Test

The water resistance tests with the ballpoint pens made as mentioned above were carried out according to the following procedure in conformity to the water resistance test specified in JIS S6039.

Writing by hand helicoidally was carried out on JIS P3201 writing paper A under the environment of 20° C., using each ballpoint pen which was confirmed to be writable. Subsequently, the written papers were dipped into water for 60 minutes in such a manner that the handwriting was soaked, then removed and dried. After the drying, the states of the handwriting were checked visually, and evaluated according to the following criteria. Results of the evaluation are shown in Table 4 below.

The Criteria
A: No bleeding of handwriting occurs.
B: The dye from handwriting bled a little, or the whole paper and dipping liquid were faintly-stained.
C: The dye bled around handwriting, or the whole paper and dipping liquid were stained.

TABLE 4

| | Examples | | | | Comparative examples | | |
|---|---|---|---|---|---|---|---|
| | 6 | 7 | 8 | 9 | 6 | 7 | 8 |
| Water resistance test | A | A | A | A | C | C | C |

[Evaluation of Whitening Resistance and Drought Resistance]

TABLE 5

| | | Examples | | | | | |
|---|---|---|---|---|---|---|---|
| | Note | 2 | 5 | 10 | 11 | 12 | 13 |
| Red dye | (2) | 7.0 | 7.0 | 7.0 | 7.0 | 7.0 | 7.0 |
| Resin A | (5) | 7.0 | 7.0 | 7.0 | 7.0 | 7.0 | 7.0 |
| Phenolic compound A | (7) | | 5.0 | | 5.0 | | 5.0 |
| Phenolic compound B | (8) | 7.0 | | 7.0 | | 7.0 | |
| Sucrose fatty acid ester A | (13) | | | | | 3.0 | 1.0 |
| Sucrose fatty acid ester B | (14) | | 1.0 | | 1.0 | | |
| Benzyl alcohol | | | | | | 3.0 | 3.0 |
| Dipropylene glycol n-propyl ether | | | | 5.0 | | | |
| Ethanol | | 59.0 | 60.0 | 54.0 | 57.0 | 56.0 | 57.0 |
| Propylene glycol monomethyl ether | | 20.0 | 20.0 | 20.0 | 20.0 | 20.0 | 20.0 |

Preparation of the Ink Compositions

Each source was mixed in an amount of the loading as described in Table 5 above and stirred at 20° C. for 3 hours to dissolve to obtain the ink composition.

Making of a Marking Pen

Each 5 g of the ink compositions obtained in the examples was stored into a commercially available marking pen exterior (PILOT CORPORATION; SCA-F) to obtain an oil-based marking pen.

Whitening Resistance Test

The polyester film was allowed to stand for 10 minutes in the constant temperature and humidity room adjusted in the condition of 20° C. and 80% RH, and the film was then checked visually whether water drops adhered onto the film due to dew condensation before five 3-mm circles were written with the marking pens made as mentioned above and then allowed to stand as it was for 10 minutes. After being allowed to stand, the handwriting were checked visually, and evaluated according to the following criteria. Results of the evaluation are shown in Table 6 below.

The Criteria
A: No whitening was observed.
B: Whitening was observed on handwriting.

Drought Resistance Test

The marking pen obtained as mentioned above was uncapped, laid in a horizontal position for 1 hour in the constant temperature and humidity room adjusted in the condition of 20° C. and 65% RH and allowed to stand for 10 hours. After being allowed to stand, the situation of writing and the states of the handwriting in writing by hand helicoidally on JIS P3201 writing paper A were checked visually, and evaluated according to the following criteria. Results of the evaluation are shown in Table 6 below.

The Criteria
A: It was possible to write in good handwriting.
B: Blur was observed on handwriting.
C: It was impossible to write.

TABLE 6

|  | Examples | | | | | |
| --- | --- | --- | --- | --- | --- | --- |
|  | 2 | 5 | 10 | 11 | 12 | 13 |
| Whitening resistance test | B | B | A | A | B | A |
| Drought resistance test (1 h) | C | A | C | A | A | A |
| Drought resistance test (10 h) | C | B | C | B | A | A |

The invention claimed is:

1. An oil-based ink composition for a writing instrument, comprising a dye, an organic solvent, and a phenolic compound of the following formula (1):

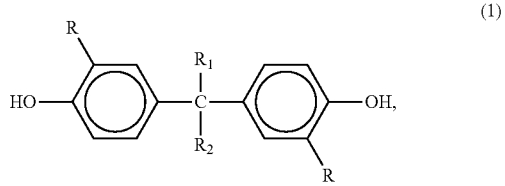

wherein:
R is each independently hydrogen or an alkyl group having 1 to 5 carbon atoms,
$R_1$ is selected from the group consisting of an alkyl group having 1 to 5 carbon atoms, a halogenated alkyl group having 1 to 5 carbon atoms, a phenyl group, a hydroxyphenyl group, and an alkyl group having 1 to 5 carbon atoms substituted by a hydroxyphenyl group, and
$R_2$ is selected from the group consisting of a halogenated alkyl group having 1 to 5 carbon atoms, a phenyl group, a hydroxyphenyl group, and an alkyl group having 1 to 5 carbon atoms substituted by a hydroxyphenyl group, and
wherein the dye and the phenolic compound are dissolved in the organic solvent, and the organic solvent is at least one selected from the group consisting of:
(i) an organic solvent having a vapor pressure at 20° C. of 10 to 50 mmHg, and
(ii) an organic solvent having a boiling point of 160 to 250° C.

2. The ink composition according to claim 1, wherein the content of the phenolic compound is 0.5 to 10% by mass based on the total mass of the ink composition.

3. The ink composition according to claim 1, wherein the dye is a solvent dye.

4. The ink composition according to claim 1, further comprising a resin.

5. The ink composition according to claim 4, wherein the resin is a ketone resin.

6. The ink composition according to claim 1, further comprising a sucrose fatty acid ester.

7. A writing instrument, comprising the oil-based ink composition for a writing instrument according to claim 1.

8. The writing instrument according to claim 7, which is selected from the group consisting of a marking pen and a ballpoint pen.

9. The ink composition according to claim 1, wherein the organic solvent is at least one selected from the group consisting of: benzyl alcohol, benzyl glycol, ethylene glycol monobutyl ether, ethylene glycol monohexyl ether, ethylene glycol monophenyl ether, diethylene glycol monoethyl ether, diethylene glycol monophenyl ether, propylene glycol monomethyl ether, propylene glycol monoethyl ether, propylene glycol monophenyl ether, dipropylene glycol monoethyl ether, dipropylene glycol monophenyl ether, tripropylene glycol monomethyl ether, tripropylene glycol monoethyl ether, tripropylene glycol monophenyl ether, methyl lactate, ethyl lactate and γ-butyrolactone.

10. The ink composition according to claim 1, wherein the organic solvent is at least one selected from the group consisting of: ethyl alcohol, n-propyl alcohol, isopropyl alcohol, n-butyl alcohol, isobutyl alcohol, sec-butyl alcohol, tert-butyl alcohol, tert-amyl alcohol, ethylene glycol monomethyl ether, ethylene glycol diethyl ether, ethylene glycol monoisopropyl ether, propylene glycol monomethyl ether, propylene glycol monoethyl ether, n-heptane, n-octane, isooctane, methylcyclohexane, ethylcyclohexane, toluene, xylene, ethylbenzene, methyl isobutyl ketone, methyl n-propyl ketone, methyl n-butyl ketone, di-n-propyl ketone, n-butyl formate, isobutyl formate, n-propyl acetate, isopropyl acetate, n-butyl acetate, isobutyl acetate, ethyl propionate, n-butyl propionate, methyl butyrate and ethyl butyrate.

11. The ink composition according to claim 1, wherein the organic solvent is at least one selected from the group consisting of: ethyl alcohol, n-propyl alcohol, isopropyl alcohol, ethylene glycol monomethyl ether, ethylene glycol diethyl ether, ethylene glycol monoisopropyl ether, propylene glycol monomethyl ether and propylene glycol monoethyl ether.

12. The ink composition according to claim 1, wherein the organic solvent is at least one selected from the group consisting of: benzyl alcohol, ethylene glycol monophenyl ether, propylene glycol n-butyl ether, dipropylene glycol methyl ether, propylene glycol diacetate, dipropylene glycol dimethyl ether, dipropylene glycol n-propyl ether, dipropylene glycol methyl ether acetate, propylene glycol phenyl ether, tripropylene glycol methyl ether, dipropylene glycol n-butyl ether, tripropylene glycol n-butyl ether, p-xylene glycol dimethyl ether, benzyl formate, benzyl acetate, benzyl propionate, benzyl butyrate and benzyl isobutyrate.

* * * * *